US007829042B2

(12) United States Patent
Halt, Sr.

(10) Patent No.: US 7,829,042 B2
(45) Date of Patent: Nov. 9, 2010

(54) PERSONAL SANITATION DEVICE

(76) Inventor: Gerald B. Halt, Sr., 27 Devon Dr., Newtown Square, PA (US) 19073

( * ) Notice: Subject to any disclaimer, the term of this patent is extended or adjusted under 35 U.S.C. 154(b) by 0 days.

(21) Appl. No.: 12/709,853

(22) Filed: Feb. 22, 2010

(65) Prior Publication Data

US 2010/0150776 A1    Jun. 17, 2010

Related U.S. Application Data

(63) Continuation of application No. 11/182,204, filed on Jul. 15, 2005, now abandoned.

(51) Int. Cl.
*A61L 2/18* (2006.01)
(52) U.S. Cl. .................. 422/292; 206/205; 206/210
(58) Field of Classification Search ............. 422/292; 424/443; 206/205, 210
See application file for complete search history.

(56) References Cited

U.S. PATENT DOCUMENTS 6,234,357 B1 * 5/2001 Lewis ...................... 222/175

FOREIGN PATENT DOCUMENTS

DE          2902005 A  *  8/1980

OTHER PUBLICATIONS

Machine translation of DE 2902005A, obtained from the EPO website (www.http://ep.espacenet.com/advancedSearch ?locale=en_ep ).*

* cited by examiner

*Primary Examiner*—Sean E Conley
(74) *Attorney, Agent, or Firm*—Volpe and Koenig, P.C.

(57) ABSTRACT

A personal sanitation device comprises a container, a substrate disposed within the container and a disinfecting agent carried by the substrate. The personal sanitation device is utilized by the user, for example, by inserting a portion of their body into the container to contact the substrate. The disinfecting agent is transferred from the substrate to the inserted body portion to sanitize that portion of the user. Objects may also be placed within the container to come in contact with the substrate so as to have the disinfecting agent transferred to said objects, thereby disinfecting them.

10 Claims, 3 Drawing Sheets

PERSONAL SANITATION DEVICE

CROSS REFERENCE TO RELATED APPLICATION

This application is a continuation of U.S. patent application Ser. No. 11/182,204, filed Jul. 15, 2005, which is incorporated by reference as if fully set forth.

FIELD OF INVENTION

The present invention is generally related to systems and methods which enhance sanitary conditions for individuals. More particularly, the present invention is a device for facilitating the immediate disinfection of a portion of user's body, after exposure to potentially infectious environments, in a manner that is both effective and discreet. In such a personal encounter for example, in church/at a social setting and one encounters a potential infectious occasion, how to deal with the hazard in a discreet but effective manner.

BACKGROUND

There is a direct correlation between the rise of modern civilization and the increase in sanitary awareness and practices among individuals. Modern medicinal techniques and pharmaceuticals have eradicated many diseases which have ravaged human societies for many millennia. Antibiotics, aspirin, current generation drugs, scanning equipment, blood analysis techniques and modern operating procedures have greatly reduced mortality rates and increased life expectancies.

Although modern medicinal techniques and pharmaceuticals have made tremendous strides toward eliminating countless diseases, humans continue to face many health threats. These health threats range from the rare to the commonplace; and from the deadly to the simply inconvenient. It is becoming increasingly difficult to battle these threatening diseases largely because many of them are caused by cross-species migrations of common diseases or new mutant strains of old diseases. Even ubiquitous threats such as common colds are becoming stronger and more resistant to treatment.

Although many diseases are transmitted via the air, via the co-mingling of blood sources, or via sexual intercourse, most diseases are transmitted by simple physical contact, either directly or through an intermediary. For example, a disease infected individual, by merely touching an object, may thereby infect that object. As subsequent individuals come into contact with the infected object, they too will become infected, and so on. This chain of infection continues as long as there are infected individuals coming into contact with inanimate objects, other people, plants or animals. In fact, given today's society, a single infected person can infect hundreds or even thousands of objects or other people in a relatively small amount of time.

One of the drawbacks of such a mass spread of a disease includes the increased probability that the disease will mutate into different strains as it spreads and migrates away from its original source. Thus, although an individual may typically gain immunity as a result of experiencing and effectively overcoming a disease, if the individual is exposed to a new or different strain of the original disease, that individual will once again become infected. It is often very difficult to break an infection, recovery, mutation, re-infection chain. Such chains of infection take a heavy toll upon both individuals and society in terms of physical, mental and economic devastation.

Many manufacturers have preyed upon society's fears of diseases by heightening awareness of the many causes of infectious diseases. It has becomes commonplace to observe commercials and advertisements which pitch products that disinfect individuals or objects. An extremely popular example of such a product includes anti-bacterial soaps. These soaps, commonly in liquid form and dispensed from a plastic container via a hand-pump, are advertised to kill almost all common forms of bacteria. Although somewhat effective, these products have a drawback in that access to a source of running water is also necessary.

More recently, sanitizing hand washes have been introduced which, although are dispersed in liquid form, do not require access to running water. These sanitizing liquids are spread by a user across an area to be disinfected, such as the user's hands. Since these sanitizing liquids are alcohol-based, they quickly evaporate after they are applied. It does not require removal by other means, such as by running water.

Although many clever schemes have been devised to sanitize body portions of individuals, namely their hands, such schemes are either inconvenient, or are socially unacceptable to implement in an expedient manner. For example, if a first individual were exposed to another individual during a handshake and that other individual is suspected of being disease infected, it would be extremely inconvenient and socially unacceptable for the first individual to dash out of the room to disinfect his hands immediately after the handshake.

Accordingly, it is desirable to have a socially responsible, discreet yet expedient and effective method for disinfecting portions of a user.

SUMMARY

The present invention is a method and apparatus for expediently, discretely and effectively sanitizing a portion of a user's body without the need for water rinse or other accompanying treatment. A flexible container having a chamber contains a flexible substrate having a disinfecting agent infused throughout. The flexible container preferably has a re-sealable opening such that the disinfecting agent may not exit the container. The disinfecting agent may be liquid, gaseous or solid, such as powder or the like, and may be infused in the substrate either throughout the entire substrate or on the surface of the substrate.

The outside of the container may be equipped with a fastening means to conveniently fasten the container to a desired part of an individual or to an individual's clothing or handbag. A user desiring to disinfect a portion of his body will place that portion of his body into the chamber to expose that portion to the disinfecting agent. Once the disinfecting agent is transferred to the portion of the body, that portion is removed and the container is re-sealed such that the disinfecting agent may not escape from the chamber. Preferably, the container is reusable, whereby enough of the agent is infused onto the substrate for several doses, or may be rechargeable such that a depleted substrate may be removed and replaced by a new substrate.

In an alternative embodiment, a chamber may include different substrates; multiple chambers may be provided, each having a different substrate; or a single substrate may have multiple disinfecting agents infused therein in order to disinfect different and complex diseases. The substrates may be selectively tailored with disinfecting agents depending upon the expected disease to which the individual is most like to be exposed.

DETAILED DESCRIPTION OF THE PREFERRED EMBODIMENTS

Figure 1:
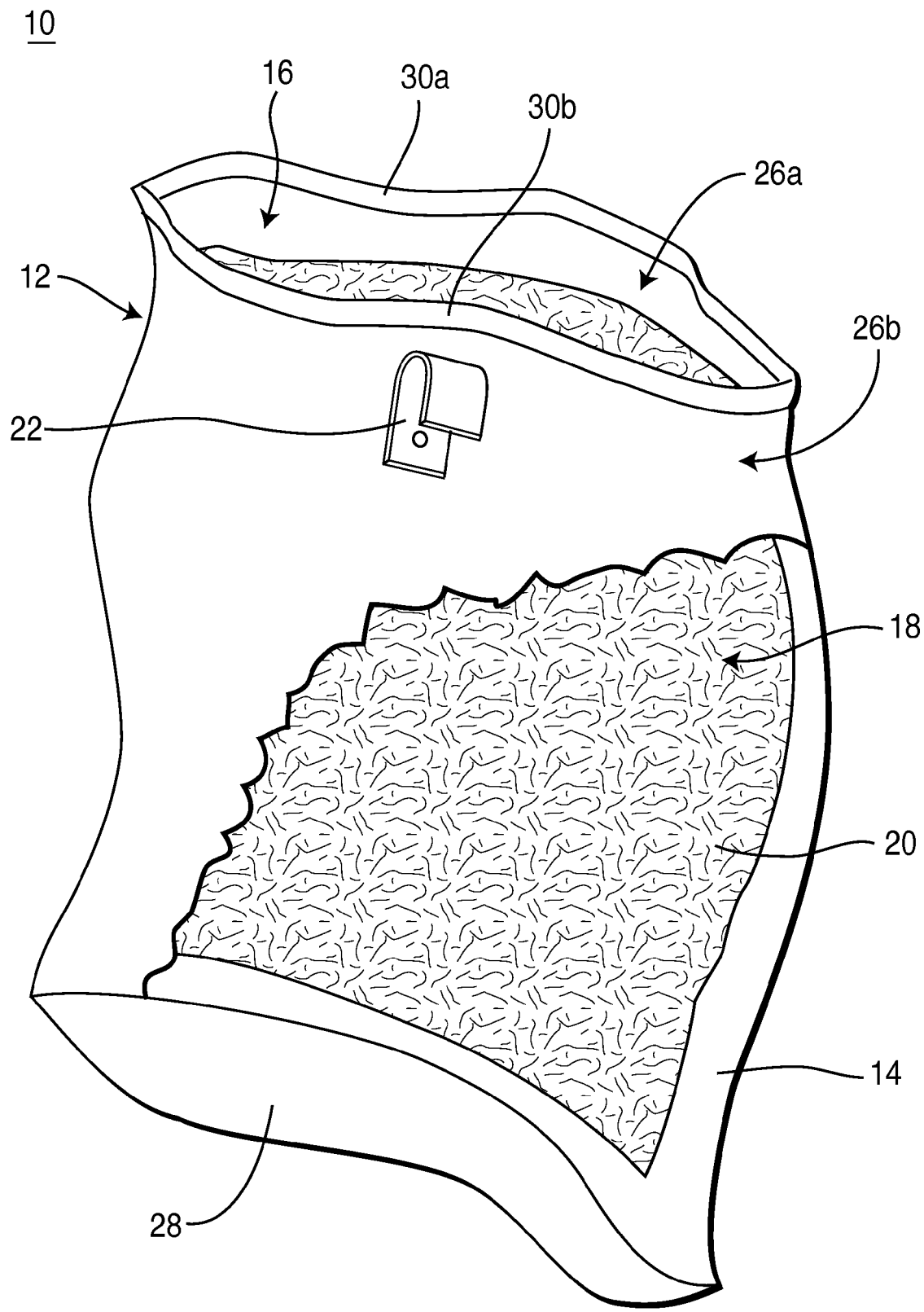
FIG. 1 is a perspective view of a personal sanitation device in accordance with the teachings of the present invention.

The present invention will be described with reference to the drawing figures wherein like numerals represent like elements throughout.

Referring to FIG. 1, a personal sanitation device 10 made in accordance with the teachings of the present invention is shown. In its simplest embodiment as shown in FIG. 1, the personal sanitation device 10 comprises a container 12 having a chamber 14, a re-sealable opening 16 and a substrate 18 having a disinfecting or anti-bacterial agent infused therein 20. A fastening means 22 is preferable coupled to the outside of the container 12.

The container 12 may be any type of flexible or inflexible receptacle for both supporting the substrate 18 and containing the disinfecting agent 20. The shape, consistency and resiliency of the container 12 may vary depending upon the type of substrate 18 and/or the consistency of the disinfectant 20 used. Since, the disinfectant 20 may be in liquid, powder, solid, gaseous or various other forms, the container 12 must be capable of accommodating such various forms and ensuring that the disinfectant 20 does not escape from the chamber 14 and become a nuisance and/or hazard to the user. With regard to the substrate 18, the container 12 need only support the substrate 18 in a manner which facilitates transfer of the disinfecting agent 20 to a portion of a user's body. Although the present invention may be utilized to disinfect any portion of a users' body, the following embodiments shall be described with reference to disinfecting a user's hands. It should be understood that such a reference should in no way be interpreted as limiting the scope of the present invention.

In an alternate embodiment, the container 12 is made of a flexible material, such as Mylar®, for example, which allows for a water-proof, vapor-proof and/or particulate-proof chamber 14. As shown in FIG. 1, the container 12 is constructed with a plurality of walls 26a, 26b, a bottom 28, and a re-sealable opening 16 that when sealed, properly contains the disinfecting agent 20 and support the substrate 18.

The re-sealable opening 16 is preferred as it provides convenient access to the disinfecting agent 20 while also preventing the agent's 20 escape from the container 12 at undesirable times or locations. The re-sealable opening 16 includes opposing complimentary fasteners 30a, 30b, one on each wall 26a, 26b, respectively, which cooperate to urge the re-sealable opening 16 closed. The opposing complementary fasteners 30a and 30b may be comprised of strips of magnetic material, a hook and loop type fastener (e.g., Velcro®), a draw-string, a zipper, a plastic snap-lock seal, or the like. The re-sealable opening 16 may also be configured without any re-sealing means. For example, if the substrate 18 and the disinfecting agent 20 are not prone to accidentally escaping through the re-sealable opening 16, such re-sealing means may not be necessary.

The substrate 18 preferable comprises a type of cloth, or absorbent material, which is flexible enough to conform to the contours of a user's hand, while providing a sturdy carrier for the disinfecting agent 20. In the embodiment shown in FIG. 1, for example, the substrate 18 is a woven cloth infused with a liquid disinfecting agent 20 such that the substrate 18 remains moist to the touch.

Figure 2:
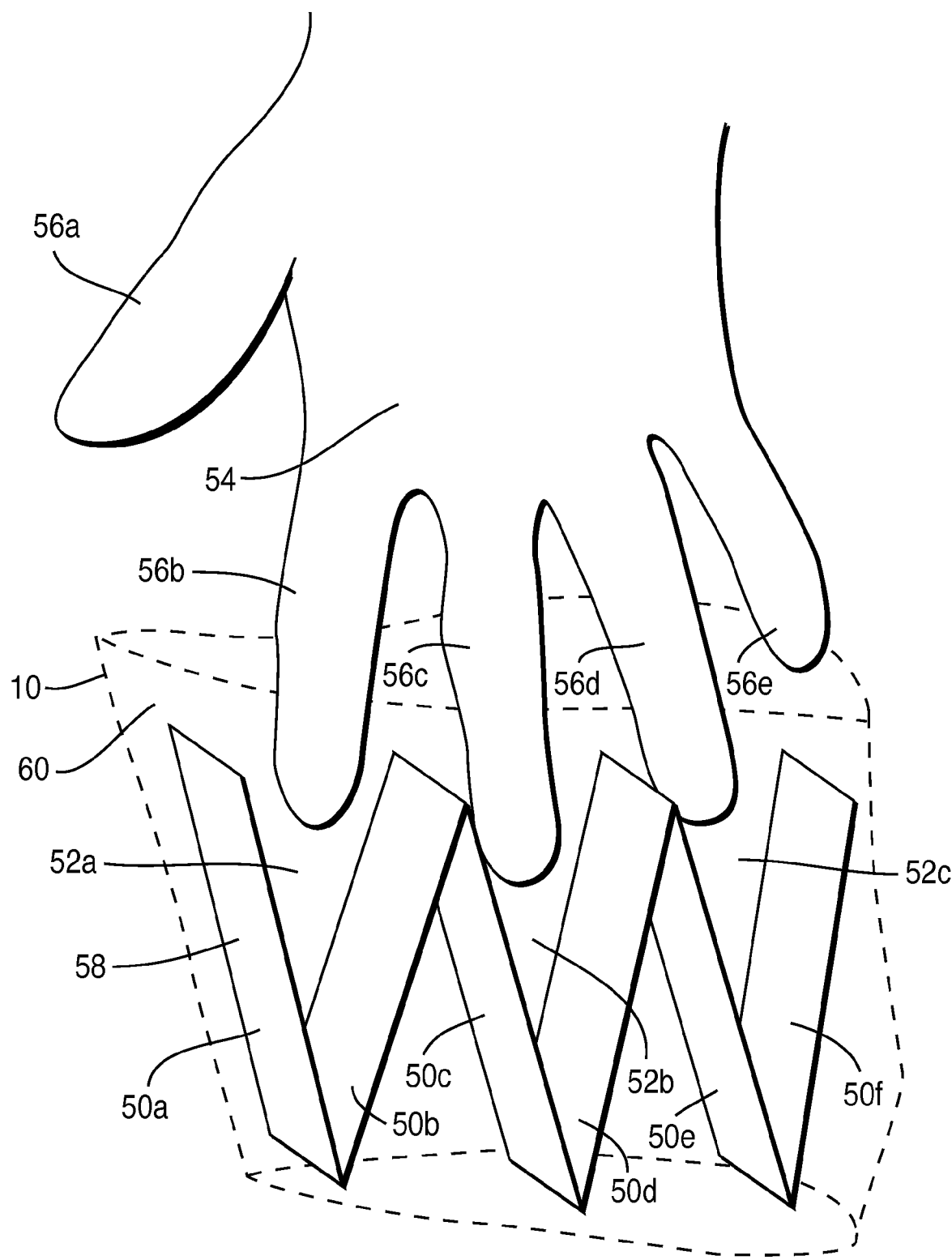
FIG. 2 is a perspective view of a user utilizing the personal sanitation device in accordance with the teachings of the present invention.

Optionally, the substrate 18 is adhered or fixed in some manner to the inside surface areas of the chamber 14. Such adhesion permits a user to, for example, disinfect all sides of his hand simultaneously because once inserted into the chamber 14, the user's hand will be contacted on all sides by the substrate 18, thereby transferring the disinfecting agent 20 from the substrate 18 onto the hand. Additionally, as shown in FIG. 2, the substrate 18 may have a plurality of baffles 50a-f, (or ruffles), which define a plurality of individual sub-chambers 52a-c or it may have a web-like consistency for retaining disinfecting agent 20. Each of these different forms of the substrate 18 will have particular advantages depending upon the form of the disinfecting agent 20 and the desired form of the personal sanitation device 10.

Referring again to FIG. 2, as a user inserts his or her hand into the device 10, which is shown in phantom as indicated by the dashed line, the individual's fingers 56a-e are inserted into individual chambers 52a-c. Accordingly, the baffles 50a-f of the substrate 58 in this embodiment conform to the fingers 56a-e of the individual's hand 54 in order to transfer the disinfecting agent (not shown) from the substrate 58 to the hand 54.

If a user desires to have a personal sized version of the sanitation device disclosed herein (i.e., a device with an extremely thin profile), a single layer of Mylar®, for example, and a thin cloth having the disinfecting agent disposed thereon will accommodate the user's desire. Although using a single layer substrate to disinfect is not ideal, a user may wish to sacrifice the efficiency of having a multi-layer substrate for discreteness in the form of a slim and easily concealable sanitation device. Alternatively, if it is imperative that the disinfecting agent be efficiently transferred onto a user's body portion, a web-like or sponge-like substrate may be utilized having disinfectant in liquid form which will soak a user's desired body portion with the liquid disinfectant. The form and construction of the substrate is not central to the present invention, it is only necessary that the disinfecting agent be transferred efficiently and as completely as possible from the substrate to the hand of the user.

Referring back to FIG. 1, the fastening means 22, which is optional, provides an effective manner of securing the disinfecting device 10 to a user or a user's property. Although shown in the form of a hook, the fastening means 22 may also be in the form of a temporary adhesive or a hook-and-loop-type fastener. Such fastening means are preferable in an embodiment wherein the personal sanitation device 10 is employed, for example, in a pocket of a user. The fastening means 22 may also be a mechanical fastener such as a safety pin or bobby pin. In essence, the fastening means 22 may be any type of fastener that secures the disinfecting device, preferably in a temporary manner, to an inside pocket of a user, to an inside portion of a user's handbag, or to any other discrete location selected by the user. Alternatively, the securing means may be a permanent fastener such as glue or thread to thereby permanently fasten the personal sanitation device 22 to user selected location.

In an alternate embodiment, a disinfecting device in accordance with the present invention is tailored specifically to a portion of a user's body which is desired to be disinfected. For example, referring back to FIG. 2, disinfecting device 10 is specifically configured to disinfect a user's hand 54. This personal sanitation device 10 can be inserted and temporarily fastened to the inside pocket or handbag of a user. When the user desires to disinfect his hand 54, the hand 54 is inserted into the chamber 60, thereby contacting the substrate 58. A disinfecting agent is then efficiently transferred from the substrate 58 to the user's hand 54.

Figure 3:
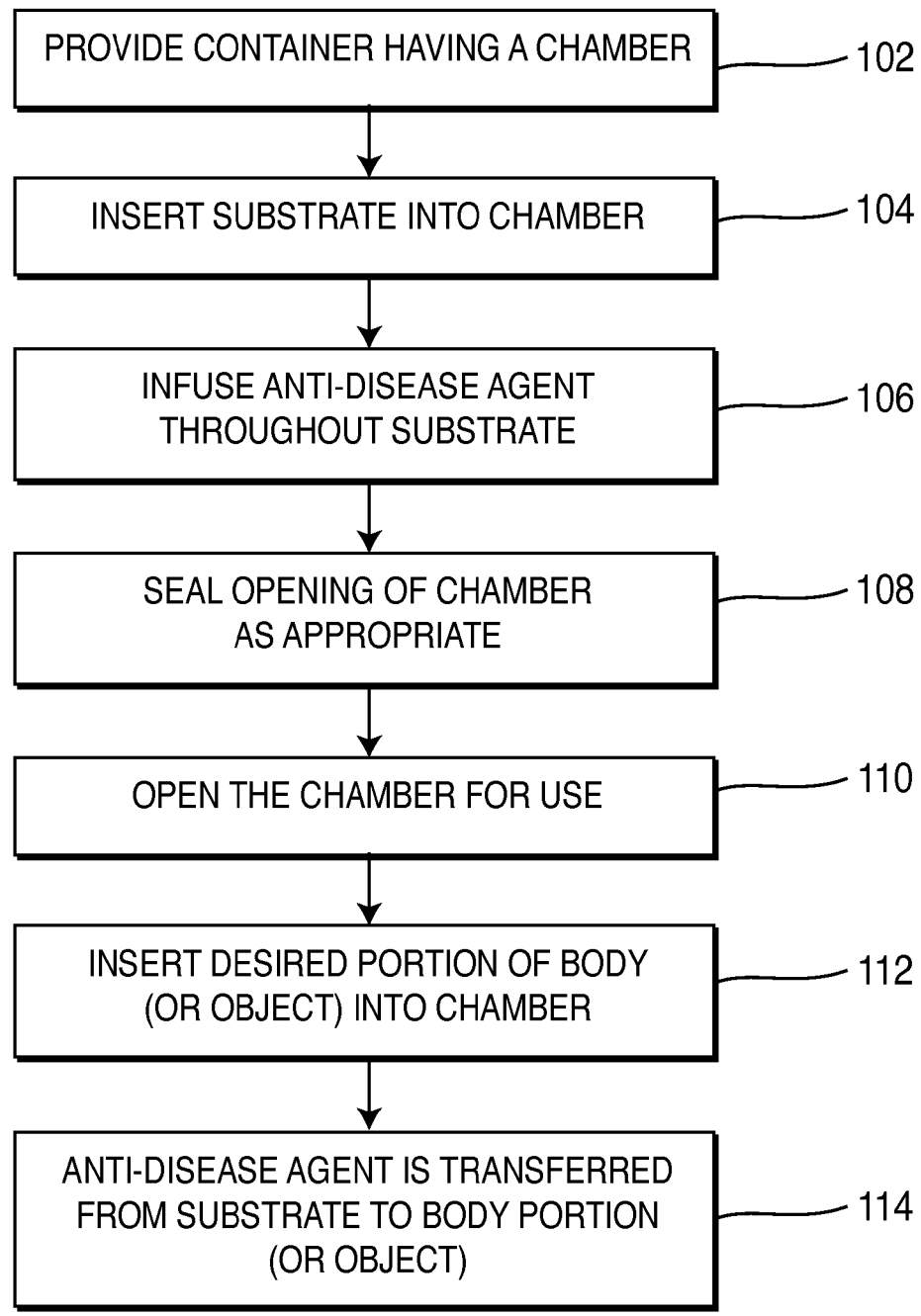
FIG. 3 is a flow diagram of a method for both setting up the personal sanitation device and utilizing the personal sanitation device in accordance with the present invention.

Referring to FIG. 3, a method 100 in accordance with the present invention is shown. The method 100 commences with providing a container suitable for holding a disinfecting agent and supporting a substrate (step 102). The substrate is inserted into the container and optionally affixed therein in step 104. The disinfecting agent is then infused throughout the substrate (step 106). It should be noted that steps 104 and 106 may be interchanged without departing from the spirit and scope of the present invention. For example, the substrate may be infused with a disinfecting agent prior to being inserted into a container.

The opening of the chamber is then closed or sealed as appropriate (step 108). When a user desires to utilize the disinfecting device, the user opens the container (step 110), inserts a desired portion of his body (or an object) into the container and provides as much contact between the body portion or the object and the substrate as possible (step 112). The disinfecting agent is then transferred from the substrate to the inserted portion of the user's body or object (step 114), thereby applying the disinfecting agent.

It should be noted that steps 102-108 relate to preparing for the use a sanitation device in accordance with the present invention and steps 110-114 relate to actually utilizing the sanitation device. Steps 102-108 may be repeated each time a substrate is depleted of its disinfecting agent.

Although the present invention has been described in detail, it is to be understood that the invention is not limited thereto, and that various changes can be made therein without departing from the spirit and scope of the invention, which is defined by the attached claims.

What is claimed is:

1. A sanitation device comprising:
    a flexible, substantially flat, outer chamber enclosing a plurality of sub-chambers, wherein each sub-chamber shape is defined by pleats of a flexible substrate within the outer chamber and the shape of each sub-chamber is a different shape than the outer chamber; and
    a disinfecting agent is infused into the flexible substrate.

2. The sanitation device of claim 1 further comprising an integrated fastening apparatus for fastening the device inside a person's clothing or other object.

3. The sanitation device of claim 1 wherein the flexible outer chamber further comprises a re-sealable opening.

4. The sanitation device of claim 3 wherein the re-sealable opening includes an apparatus selected from a group consisting of magnetic strips, a hook-and-loop fastener, a drawstring, a zipper, and a snap-lock seal.

5. The sanitation device of claim 1 wherein the substrate is removable.

6. The sanitation device of claim 5 wherein the substrate is re-infusable with the disinfecting agent once the disinfecting agent is depleted from the substrate.

7. The sanitation device of claim 1 wherein the disinfecting agent is a liquid.

8. The sanitation device of claim 1 wherein the disinfecting agent is a suspension.

9. The sanitation device of claim 1 wherein the shape of the sub-chambers conform to fingers of a hand.

10. The sanitation device of claim 1 wherein the outer chamber is Biaxially-oriented polyethylene terephthalate (BoPET) material.

* * * * *